(12) United States Patent
Herbsommer et al.

(10) Patent No.: US 9,529,334 B2
(45) Date of Patent: Dec. 27, 2016

(54) ROTATIONAL TRANSITION BASED CLOCK, ROTATIONAL SPECTROSCOPY CELL, AND METHOD OF MAKING SAME

(71) Applicant: Texas Instruments Incorporated, Dallas, TX (US)

(72) Inventors: Juan Alejandro Herbsommer, Allen, TX (US); Benjamin S. Cook, Dallas, TX (US); Phillip Nadeau, Cambridge, MA (US); Simon Joshua Jacobs, Lucas, TX (US); Django Earl Trombley, Dallas, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 14/674,197

(22) Filed: Mar. 31, 2015

(65) Prior Publication Data
US 2016/0291549 A1    Oct. 6, 2016

(51) Int. Cl.
| | |
|---|---|
| *H03L 7/26* | (2006.01) |
| *G04F 5/14* | (2006.01) |
| *G01N 29/44* | (2006.01) |
| *G01N 29/36* | (2006.01) |

(52) U.S. Cl.
CPC ............. *G04F 5/145* (2013.01); *G01N 29/36* (2013.01); *G01N 29/44* (2013.01); *G04F 5/14* (2013.01); *H03L 7/26* (2013.01)

(58) Field of Classification Search
CPC .......... H03L 7/26; G01N 29/36; G01N 29/44; G04F 5/14
USPC ..................................... 331/3, 94.1
See application file for complete search history.

(56) References Cited

U.S. PATENT DOCUMENTS

| | | | |
|---|---|---|---|
| 3,388,339 A | 6/1968 | Malnar et al. | |
| 8,217,724 B2 | 7/2012 | Briggs et al. | |
| 8,624,682 B2 | 1/2014 | Ridley et al. | |
| 8,906,470 B2 | 12/2014 | Overstolz et al. | |
| 2006/0022761 A1 | 2/2006 | Abeles et al. | |
| 2007/0247241 A1* | 10/2007 | Braun | G04F 5/14 331/94.1 |
| 2010/0156547 A1 | 6/2010 | McGuyer et al. | |
| 2010/0189605 A1* | 7/2010 | Schmid | B01L 3/508 422/552 |
| 2013/0015850 A1 | 1/2013 | Lindorfer et al. | |

(Continued)

OTHER PUBLICATIONS

International Search Report and Written Opinion for PCT/US2016/025445 mailed Jun. 30, 2016.

*Primary Examiner* — Arnold Kinkead
(74) *Attorney, Agent, or Firm* — Michael A. Davis, Jr.; Charles A. Brill; Frank D. Cimino

(57) ABSTRACT

Described examples include a millimeter wave atomic clock apparatus, chip scale vapor cell, and fabrication method in which a low pressure dipolar molecule gas is provided in a sealed cavity with a conductive interior surface forming a waveguide. Non-conductive apertures provide electromagnetic entrance to, and exit from, the cavity. Conductive coupling structures formed on an outer surface of the vapor cell near the respective non-conductive apertures couple an electromagnetic field to the interior of the cavity for interrogating the vapor cell using a transceiver circuit at a frequency that maximizes the rotational transition absorption of the dipolar molecule gas in the cavity to provide a reference clock signal for atomic clock or other applications.

15 Claims, 9 Drawing Sheets

(56) References Cited

U.S. PATENT DOCUMENTS

| | | |
|---|---|---|
| 2013/0147472 A1 | 6/2013 | French et al. |
| 2013/0176703 A1 | 7/2013 | Hopper et al. |
| 2014/0347074 A1 | 11/2014 | Nadeau |
| 2014/0368377 A1 | 12/2014 | Nadeau et al. |
| 2014/0373599 A1 | 12/2014 | Trombley et al. |
| 2015/0001694 A1 | 1/2015 | Hopper et al. |
| 2015/0027908 A1 | 1/2015 | Parsa et al. |
| 2015/0028866 A1 | 1/2015 | Parsa et al. |

* cited by examiner

ROTATIONAL TRANSITION BASED CLOCK, ROTATIONAL SPECTROSCOPY CELL, AND METHOD OF MAKING SAME

TECHNICAL FIELD

This disclosure relates generally to vapor cells, and more particularly to rotational transition based clocks, vapor cells therefor and fabrication methods.

BACKGROUND

Atomic clocks use the frequency of the electronic transition of an alkali metal vapor as a frequency reference. Alkali metal gasses, such as Cesium, Rubidium or other atom with a single electron in the outer shell, undergo optical transitions at very high discrete frequencies in the hundreds of GHz (optical wavelengths of around 800-900 nm). Atomic clocks determine the frequency of the electronic transition of a vaporized alkali atom by optically interrogating the gas over a bandwidth including the transition frequency, with the absorption detected at the transition frequency identifying the absolute frequency reference for the clock. Chip-scale Alkali vapor atomic clocks typically use an optical transparency peak (e.g., coherent population trapping) verses an absorption null (incoherent microwave pumping) to lock a reference frequency. Such electronic transition clocks, however, require thermal stability of the laser optical source and the electronic transition vapor cell itself requires stable gas temperature, and heating circuitry is therefore often needed. Electronic transition clocks include a modulator to modulate the laser signal, and multiple complex electronic control loops are required for operation. Also, electronic transition atomic clocks typically require a coil around the cell or other magnetic shielding to shield external magnetic fields to provide a constant magnetic field at the physics cell inside the shield in order to break degeneracy of ground-state Zeeman levels. Accordingly, electronic transition clocks suffer from relatively high power consumption, as well as additional cost and space for the necessary circuitry including the laser, modulator, photo detector and other optical components such as collimators, isolators, polarizers, lenses, etc.

SUMMARY

In described examples, millimeter wave atomic clock apparatus uses rotational transition of dipolar molecular vapor, as well as chip scale vapor cell apparatus and fabrication techniques 1, in which a dipolar molecule gas is sealed in a cavity with a conductive interior surface forming a waveguide, and the cell includes first and second non-conductive apertures allowing electromagnetic entrance to, and exit from, the cavity. Conductive coupling structures on the vapor cell outer surface near the apertures couple an electromagnetic field to the interior of the cavity. This facilitate sub terahertz electromagnetic interrogation using a transceiver circuit to identify the quantum rotational transition frequency that maximizes the electromagnetic absorption of the dipolar molecule gas in the cavity to provide a reference clock signal.

DETAILED DESCRIPTION

Figure 1:
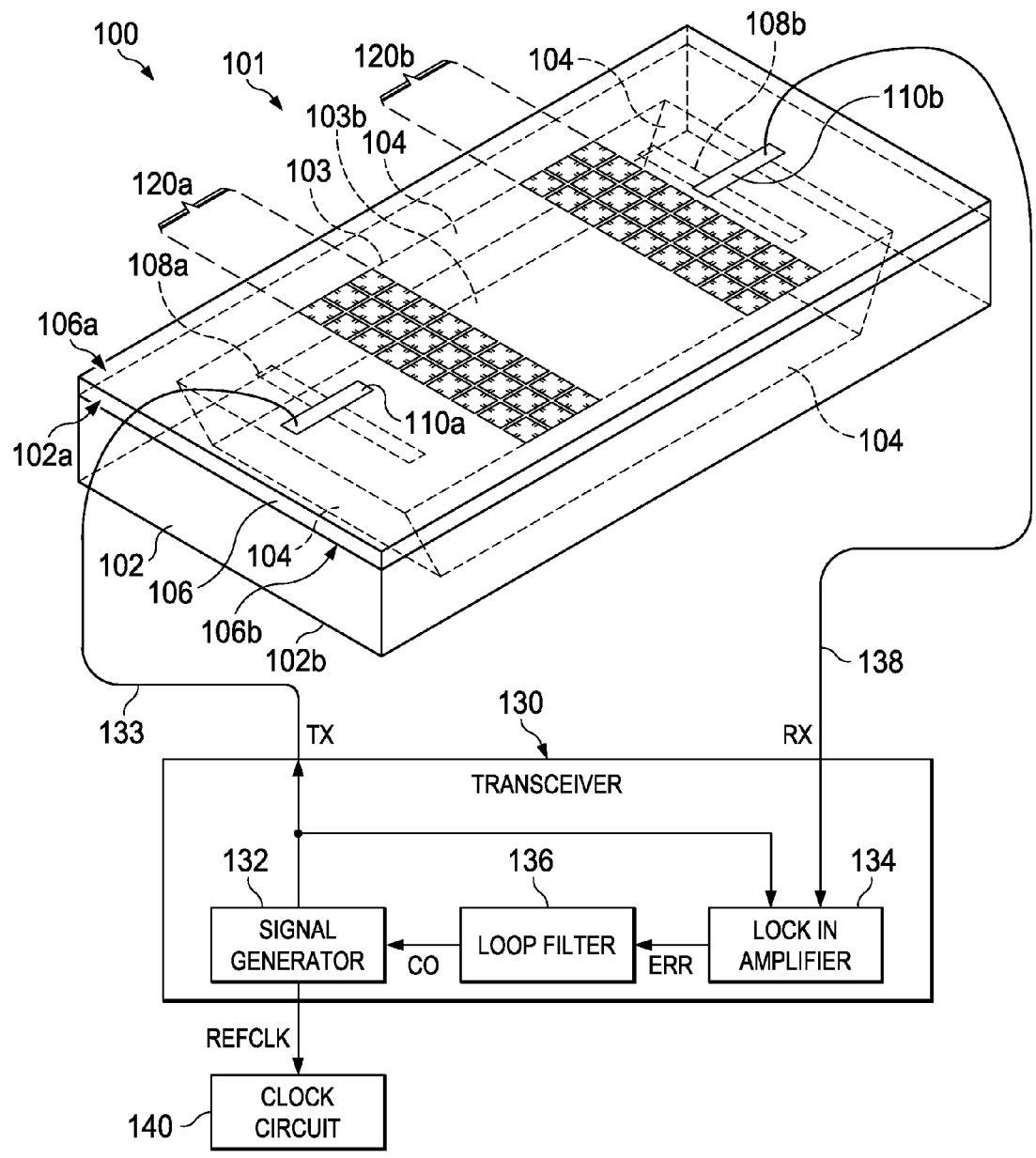
FIG. 1 is a partial perspective view of a rotational transition based clock apparatus with a dipolar molecule vapor cell and an associated transceiver circuit for providing a reference clock signal.

In the drawings, like reference numerals refer to like elements throughout, and the various features are not necessarily drawn to scale. Novel, compact, energy efficient rotational transition clock systems, along with simple low-cost packaging and fabrication processes may be employed to facilitate implementation of wafer scale or chip scale rotational spectroscopy cells or vapor cells in a silicon-based process for use in atomic clocks and other applications. Dipolar gas molecules (e.g., water or $H_2O$) have defined quantum rotational state transitions, and that such molecules absorb energy at a very repeatable frequency when transitioning between rotational states. For example, water absorbs energy based on quantum rotational state transitions at 183.31 GHz. In at least one example, clock apparatus 100 includes vapor cells 101 fabricated in a silicon-based process, which do not require lasers, modulators, photodetectors and other optical components and associated temperature stabilization (e.g., heating) components as was the case with conventional electronic transition based atomic clocks. Further, the chip scale vapor cells 101 can be combined with, or interconnected with, simple transceiver circuitry to implement a cost effective and power efficient transition based atomic clock operable at much lower frequencies than electronic transition atomic clock designs using a single relatively simple control loop, thus mitigating the complex control techniques required for conventional atomic clock architectures.

FIG. 1 shows a clock apparatus or system 100 including a vapor cell structure 101, referred to herein as a physical cell, formed in this example from first and second substrates 102 and 106. The cell 101 includes a chamber or cavity 103 with a sealed interior enclosing a dipolar molecule material gas, for example, water ($H_2O$) or any other dipolar molecule gas at a relatively low gas pressure inside the cavity 103. Non-limiting examples of suitable electrical dipolar material gases include water, acetonitrile ($CH_3CN$) and hydrogen cyanide (HCN). As shown in FIG. 1, the clock 100 further includes a transceiver 130 with a transmit output 133 for providing an electrical transmit signal (TX) to the vapor cell 101, as well as a receiver input 138 for receiving an electrical input signal (RX) from the vapor cell 101. Unlike electronic transition vapor cells, the rotational transition vapor cell structure 101 does not require optical interrogation, and instead operates through electromagnetic interrogation via the transmit and receive signaling TX, RX provided by the transceiver 130.

The sealed cavity 103 includes a conductive interior cavity surface, as well as first and second non-conductive apertures 108a and 108b formed in the interior cavity surface for providing an electromagnetic field entrance and an electromagnetic field exit, respectively. In one example, the apertures 108 magnetically couple into the TE10 mode of the waveguide cavity 103. In other examples, the apertures 108 excite higher order modes. A first conductive coupling structure 110a is formed on an outer surface 106a of the vapor cell 101 proximate the first non-conductive aperture 108a. In the example 100, the first coupling structure 110a is a conductive strip formed on the upper surface 106a of the upper substrate 106 which overlies (e.g., and crosses over) the corresponding first non-conductive aperture 108a for providing an electromagnetic interface to couple a magnetic field into the interior of the cavity 103 based on the transmit signaling TX from the transceiver output 133. A second coupling structure 110b is formed proximate the second non-conductive aperture 108b for providing an electromagnetic field exit from the cavity 103 to couple the electromagnetic field with the transceiver RX input 138. The proximate location of the conductive coupling structures 110 and the corresponding non-conductive apertures 108 advantageously provides electromagnetically transmissive paths through the second or upper substrate 106, which can be any electromagnetically transmissive material. In some examples, one or more conductive electronic bandgap (EBG) structures 120 are formed on the outer surface 106a of the vapor cell 101, spaced from the conductive coupling structures 110. In operation, the EBG structures 120 attenuate electromagnetic wave coupling along the vapor cell outer surface 106a between the transmit and receive coupling structures 110a and 110b, respectively. In other examples, the EBG structures 120 may be omitted.

A lower side 106b of the second substrate 106 is substantially or completely plated with conductive material (e.g., copper 94 as shown in FIGS. 9-12 below) and the apertures 108 are etched to provide non-conductive windows or apertures 108 in the lower second side 106b, with the coupling structures 110 and any included EBG structures 120 being formed of conductive material (e.g., copper) on the upper side 106a of the second substrate 106. In one example, two EBG structure patterns 120a and 120b are provided, which can be any suitable shape and configuration for electromagnetic attenuation on the upper surface 106a of the vapor cell 101. The cell cavity 103 is defined by the lower side 106b of the upper substrate 106, as well as by sidewalls 104 and a cavity bottom 103b formed in the first (lower) substrate 102, which can be any suitable material, such as silicon, as further shown in FIG. 8 below.

Figure 6:
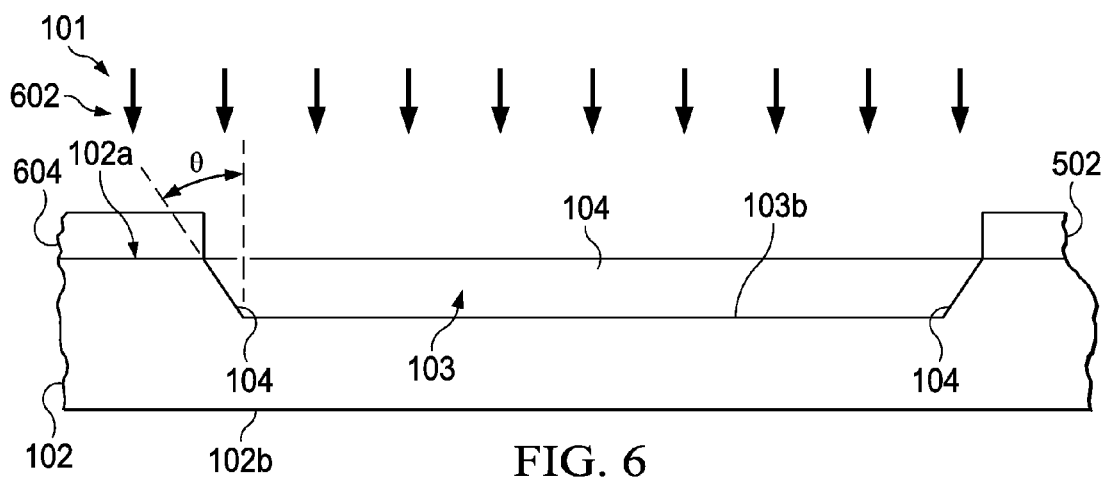
FIG. 6 is a partial side elevation view of a first substrate undergoing an etch process to form a cavity.

In the example of FIG. 1, the first or lower substrate 102 includes a top or first side 102a into which the cavity sidewalls 104 and a cavity bottom 103b are formed, for example, by etching (e.g., FIG. 6 below). The cell cavity 130 in this example extends along a substantially linear axis from a first end to a second end, with the first aperture 108a proximate the first end and the second aperture 108b proximate the second end. Another example described further below in connection with FIG. 18 has more than two apertures 108 formed in the cavity conductive surface.

A variety of different cavity sizes and shapes may be used in other examples. One suitable non-limiting example provides a generally rectangular cavity shape with a top width of approximately 1.5 mm and an etch depth of 0.5 mm with a first mode beginning at 120 GHz, a second mode beginning at 230 GHz and a third mode at 290 GHz. Other shapes, sizes and configurations of cell cavities 103 are possible. For example, FIG. 17 below illustrates another vapor cell example 101 having a meandering cavity shape having a length dimension L extending along a non-linear axis from a first end proximate the first aperture 108a to a second end proximate the second aperture 108b.

Figure 15:
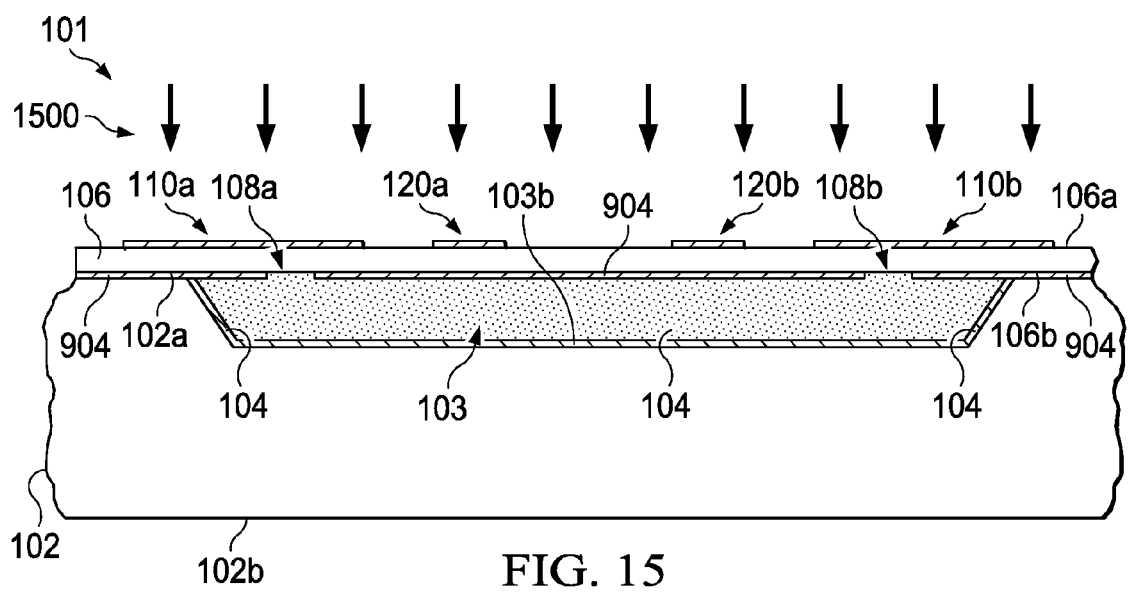
FIG. 15 is a partial side elevation view of the first and second substrates undergoing a wafer bonding process to seal the cavity in a controlled low-pressure environment and provide a chip scale vapor cell with dipolar molecular gas inside the sealed cavity.

As shown in FIG. 1, the second side 106b of the second substrate 106 is mounted to the first side 102a of the first substrate 102 in order to form the cavity 103 including the sealed interior with the conductive interior cavity surfaces extending at least partially along the cavity sidewall or sidewalls 104, the cavity bottom 103b and the lower side 106b of the second substrate 106, with the lower second side 106b of the second substrate 106 providing a cavity top with a conductive surface 94 (FIG. 15 below). In some examples, the only non-conductive cavity surfaces are the non-conductive apertures 108 on the bottom 106b of the upper substrate 106. Other non-conductive portions are possible within the cavity 103 in some examples. In the illustrated example, the conductive interior cavity surfaces are plated or otherwise provided with copper or other metal material having a thickness greater than a skin depth at the frequency of the transmit output signal TX. The first and second substrates 102 and 106 are joined together in certain examples by wafer bonding processing (e.g., FIG. 15 below) in a process chamber with a controlled low-pressure environment to provide the dipolar molecule gas (e.g., $H_2O$) in the cavity 103 during wafer bonding at a pressure of about 1 mbar or less. In certain examples, the dipolar molecule gas is at a low pressure of about 0.1 mbar or less and about 0.01 mbar or more inside the sealed interior of the cavity 103. In general, the pressure can be tailored for a given design, where the transition width depends primarily on pressure broadening and Doppler broadening. The pressure broadening factor is linear with pressure, whereas the Doppler broadening is constant with pressure. Accordingly there is one desired pressure at which further pressure reduction provides no further transition frequency width reduction due to the Doppler effect, and further pressure reduction would reduce the magnitude of the peak transition and the width will be the same, thereby degrading detection and transition tracking.

Gettering agents may be introduced during wafer bonding to include getters within the resulting vapor cavity 103 to getter any contaminants that may be present during the wafer bonding process and/or which may leak into the cavity 103 over time.

In certain examples, the cell 101 may include pattern heaters with temperature sensors formed on or in the cell bottom 102b for stabilizing the cell temperature. Such heating elements may be operable to boil off any vapor absorbed on the chamber sidewalls 104 thereby facilitating pressure stability in operation.

The transceiver circuit 130 in certain implementations is implemented on or in an integrated circuit (not shown), to which the vapor cell 101 is electrically coupled for transmission of the TX signal via the output 133 and for receipt of the RX signal via the input 138. The transceiver 130 is operable when powered for providing an alternating electrical output signal TX to the first conductive coupling structure 110a for coupling an electromagnetic field to the interior of the cavity 103, as well as for receiving the alternating electrical input signal RX from the second conductive coupling structure 110b representing the electromagnetic field received from the cavity 103. The transceiver circuit 130 is operable for selectively adjusting the frequency of the electrical output signal TX in order to reduce the electrical input signal RX by interrogation to operate the clock 100 at a frequency which substantially maximizes the molecular absorption through rotational motor state transitions, and for providing a reference clock signal REFCLK to a clock circuit 140 at the frequency of the TX output signal.

In certain examples, the transceiver 130 includes a signal generator 132 with an output 133 electrically coupled with the first conductive coupling structure 110a for providing the alternating electrical output signal TX, and for providing the reference clock signal REFCLK at the corresponding transmit output frequency. The transceiver 130 also includes a lock-in amplifier circuit 134 with an input 138 coupled with the second conductive coupling structure 110b for receiving the RX signal, and the lock-in amplifier operates for providing an error signal ERR representing a difference between the RX signal and the electrical output signal TX. In one example, the lock-in amplifier circuit 134 provides the error signal ERR as an in-phase output, and the error signal ERR is used as an input by a loop filter or controller circuit 136 for providing a control output signal CO to the signal generator 132 for selectively adjusting the TX output signal frequency to maintain this frequency at a peak absorption frequency of the dipolar molecular gas inside the sealed interior of the cavity 103. In some examples, the RF power of the TX and RX loop is controlled so as to avoid or mitigate stark shift affects.

The electromagnetic coupling via the non-conductive apertures 108 and corresponding conductive coupling structures 110 facilitates electromagnetic interrogation of the dipolar gas within the cell cavity 103, and the system 100 avoids the cost, complexity, power consumption and optical transmission problems associated with conventional electronic transition atomic clock vapor cells. In one non-limiting form of operation, the clock system 100 operates with the signal generator 132 transmitting alternating signals TX at full transmission power at various frequencies within a defined band around a suspected quantum absorption frequency at which the transmission efficiency of the vapor cell 101 is minimal (absorption is maximal). For example, the quantum absorption frequency associated with the dipolar water molecule is 183.31 GHz. When the system operates at the quantum frequency, a null or minima is detected at the receiver via the lock-in amplifier 134, which provides the error signal ERR to the loop filter 136 for regulation of the TX output signal frequency via the control output CO signal provided to the signal generator 132. The rotational quantum frequency of the dipolar molecule gas in the vapor cell cavity 103 is generally stable with respect to time (does not degrade or drift over time), and is largely independent of temperature and a large number of other variables. As a result, the clock system 100 need not include thermal or other stabilizing circuitry found in electronic transition based atomic clocks.

The transceiver system 130 in one example operates the signal generator 132 to initially sweep the transmission output frequency through a band known to include the quantum frequency of the cell 101 (e.g., transitioning upward from an initial frequency below the suspected quantum frequency, or initially transitioning downward from an initial frequency above the suspected quantum frequency, or other suitable sweeping technique or approach). The transceiver circuit 130 monitors the received energy via the input 138 coupled with (e.g., electrically connected to) the second conductive coupling structure 110b in order to identify the transmission frequency associated with peak absorption by the gas in the cell cavity 103 (e.g., minimal reception at the receiver). Once the quantum absorption frequency is identified, the loop filter or controller 136 moves the source signal generator transmission frequency close to that absorption frequency (e.g., 183.31 GHz), and modulates the signal at a very low frequency (e.g., left and right along the frequency axis in FIG. 4) as necessary in order to regulate operation around the null or minima in the transmission efficiency representing the ratio of the received energy to the transmitted energy, with the loop filter 136 providing negative feedback in a closed loop operation to maintain the signal generator 132 operating at a TX frequency corresponding to the quantum frequency of the cavity dipolar molecule gas.

The inventors have appreciated that, unlike optically interrogated electronic transition type atomic clocks using alkali metal gas vapor cells, the disclosed rotational transition based atomic clock 100 uses the rotational transition of dipolar molecules like water, where the frequency of this type of quantum transition is in the sub-THz range. In this regard, while electronic transition type atomic clocks need to excite the alkali metal gas with a laser operating at hundreds of THz (wavelengths in hundreds of nanometers), the millimeter wave clock 100 interrogates the gas with mm-wave radiation induced by a RF transceiver circuit 130. The clock 100 in certain examples can lock-in to the rotational quantum molecular transition with typical Alan deviation of 1e-10 to 1e-11 over 100 seconds averaging. In some examples, the disclosed rotational transition based atomic clock apparatus 100 works at sub THz frequency, and is therefore a simpler, lower cost and lower power solution for providing a stable reference clock signal.

In steady state operation, the lock-in amplifier 134 and the loop filter 136 maintain the transmitter frequency at the peak absorption frequency of the cell gas. In one non-limiting example, the loop filter 136 provides PID control using a derivative of the frequency error as a control factor for lock-in detection and closed loop regulation. At the bottom of the null in the transmission coefficient curves of FIG. 4, the derivative is zero and the loop filter 136 feeds the derivative back as a DC control output signal CO to the signal generator 132. This closed loop operates to keep the signal generator transmission output frequency at the peak absorption frequency of the cell gas using lock-in differentiation based on the RX signal received from the cell 101. As shown in FIG. 1, further clock circuitry 140 receives a reference clock signal REFCLK for use by frequency dividers, etc. for generating system clocks used in a host system (not shown).

Figure 2:
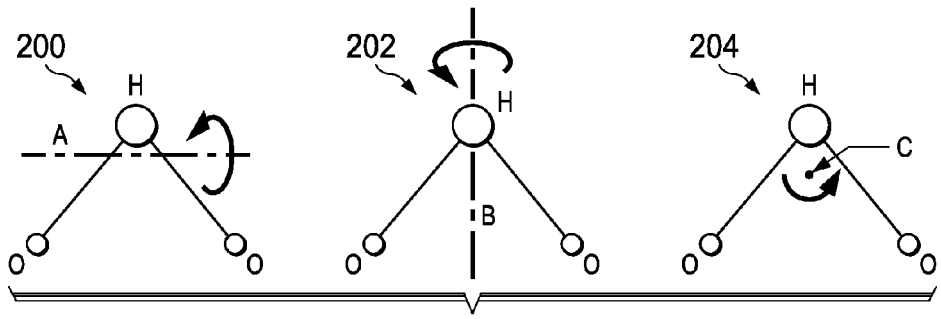
FIG. 2 is a simplified diagram of three rotational modes of a dipolar water molecule.
Figure 3:
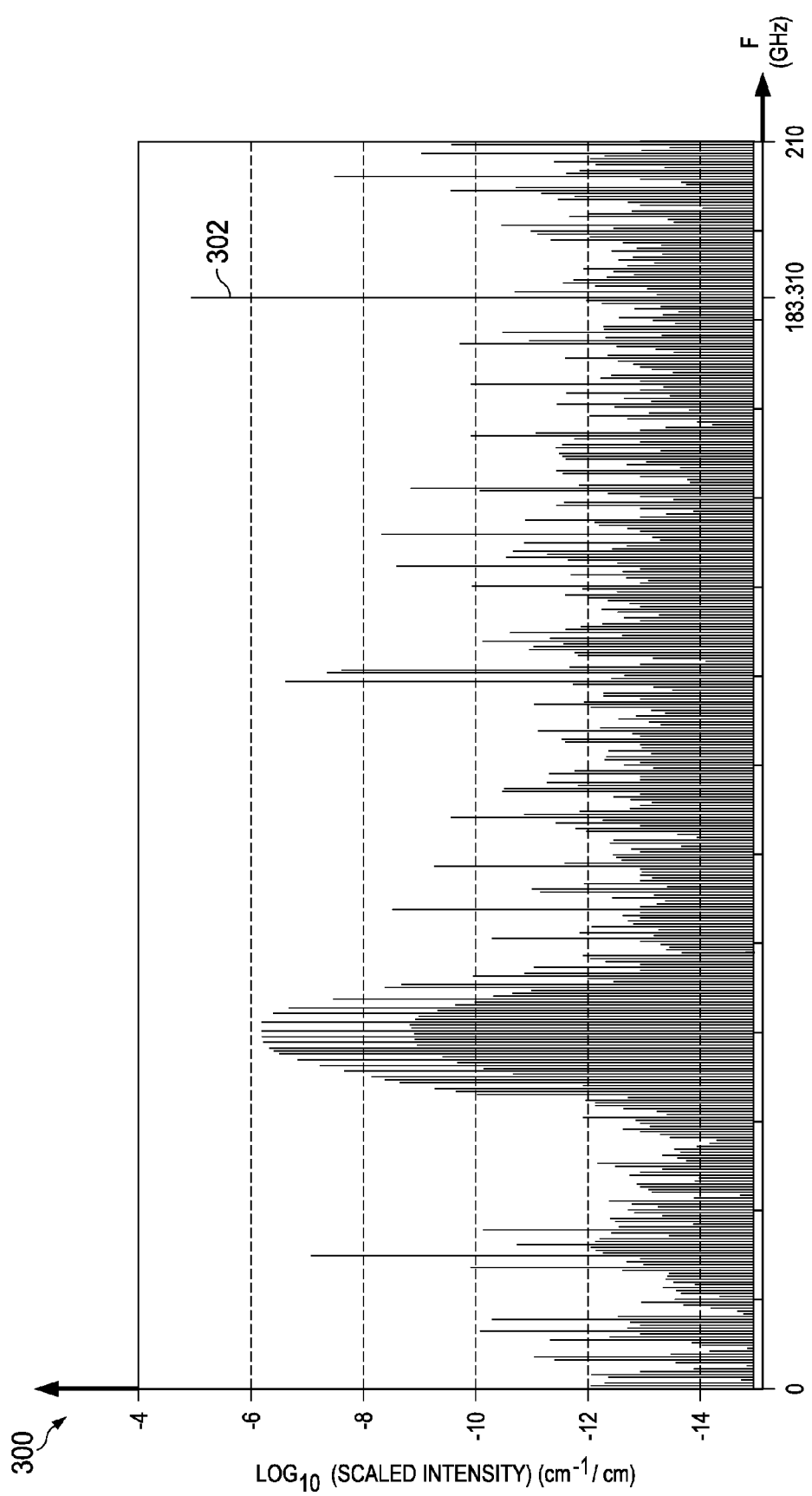
FIG. 3 is a graph of rotational modes of a variety of gases as a function of frequency with high relative absorption for low-pressure water vapor at an identifiable quantum transition frequency.
Figure 4:
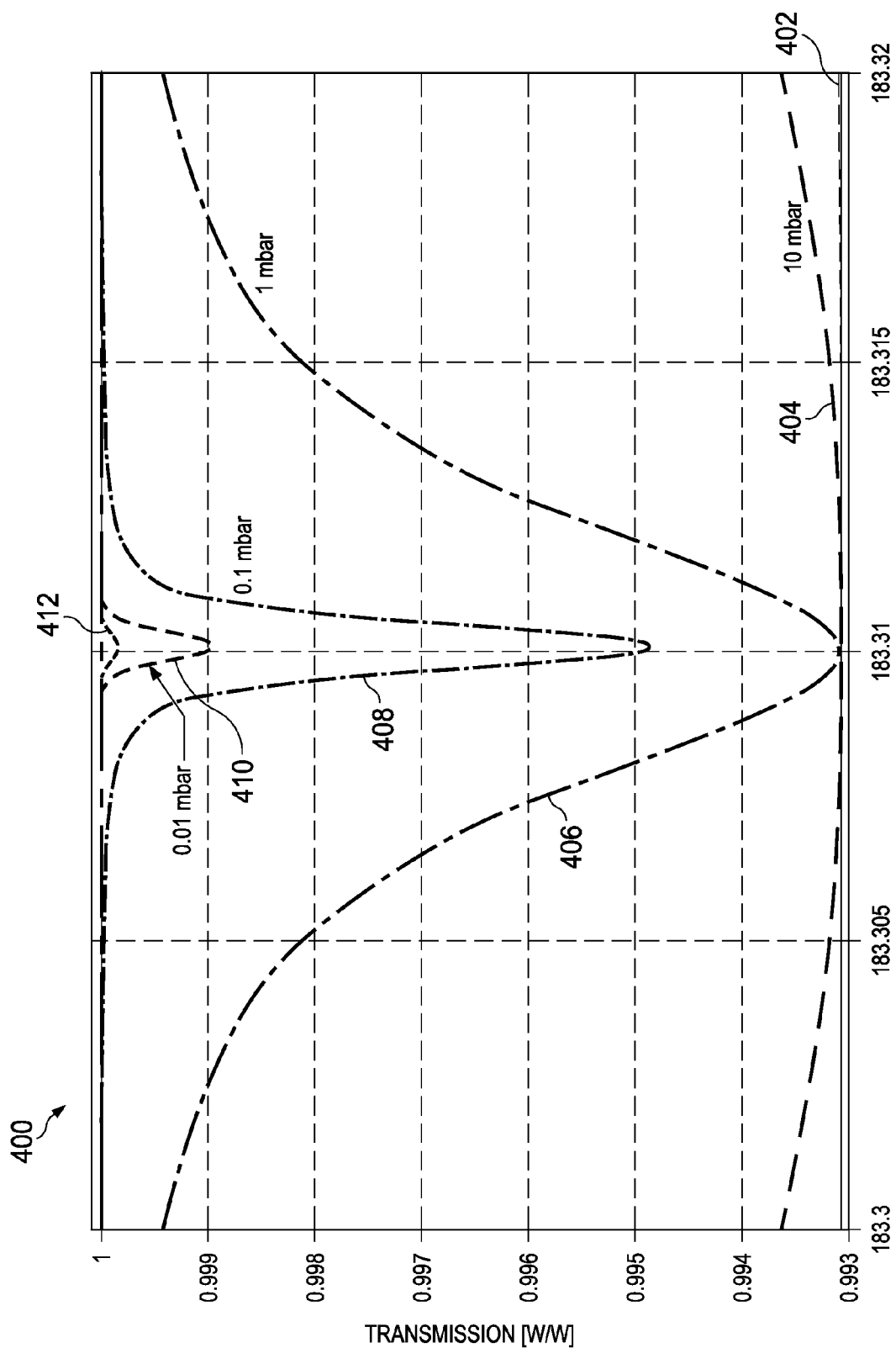
FIG. 4 is a graph of transmission coefficient through the cell vs frequency of interrogation for different pressure levels inside the cell.

Referring also to FIGS. 2-4, FIG. 2 provides illustrations 200, 202 and 204 respectively showing three rotational modes of a dipolar water molecule along three orthogonal axes, and FIG. 3 shows a graph 300 of relative absorption for rotational modes of a variety of gases as a function of electromagnetic wave frequency. As seen in FIG. 3, the absorption line 302 corresponding to water indicates that this dipolar molecule $H_2O$ has high relative absorption for low-pressure water vapor at an identifiable quantum transition frequency (183.31 GHz) and has a much higher absorption than the rest of the gases at the same frequency range.

The graph 400 in FIG. 4 illustrates transmission coefficient through the cell as a function of interrogation frequency for different pressure levels inside the cell, where curves 402, 404, 406, 408, 410 and 412 correspond to various cavity pressures, including pressure greater than 10 mbar (curve 402), cavity pressure of 10 mbar (404), 1.0 mbar (curve 406), 0.1 mbar (curve 408), 0.01 mbar (curve 410), and a pressure below 0.01 mbar (curve 412). The inventors have found that specific implementations for dipolar water molecular gas in the cavity 103 advantageously facilitate identification and lock-in at the peak absorption frequency in operation of the clock system 100. For example, a cavity pressure of about 1 mbar or less, such as about 0.1 mbar or less and about 0.01 mbar or more provides particular operational advantages in the case of water vapor. The cavity pressure in certain implementations is controlled during the bonding process while mounting the second substrate 106 to the top side of the first substrate 102 in FIG. 1 to provide a sealed cavity 103 in a low-pressure processing chamber. As seen in FIG. 4, the quantum transition frequency identified by the peak absorption (null or relative minima in the absorption efficiency curves of FIG. 4) increases (e.g., becomes wider) with increasing cavity pressure. The inventors have appreciated that operation at a higher cavity pressure (e.g., room pressure) may lead to difficulties identifying the efficiency minima, and therefore difficulties in lock-in to the quantum frequency of the cell gas. Accordingly, specific examples provide for reducing the pressure inside the cavity 103 in order to increase the quality factor of the peak in absorption, for example, curves 406, 408 and 410 in FIG. 4. The inventors have also appreciated that further reductions in pressure, however, lead to diminishing returns due to increased prevalence of Doppler and other factors relating to molecules hitting the cavity sidewalls 104, and that the magnitude of the absorption peak decreases with reduced pressure due to interrogation of fewer dipolar molecules.

Figure 5:
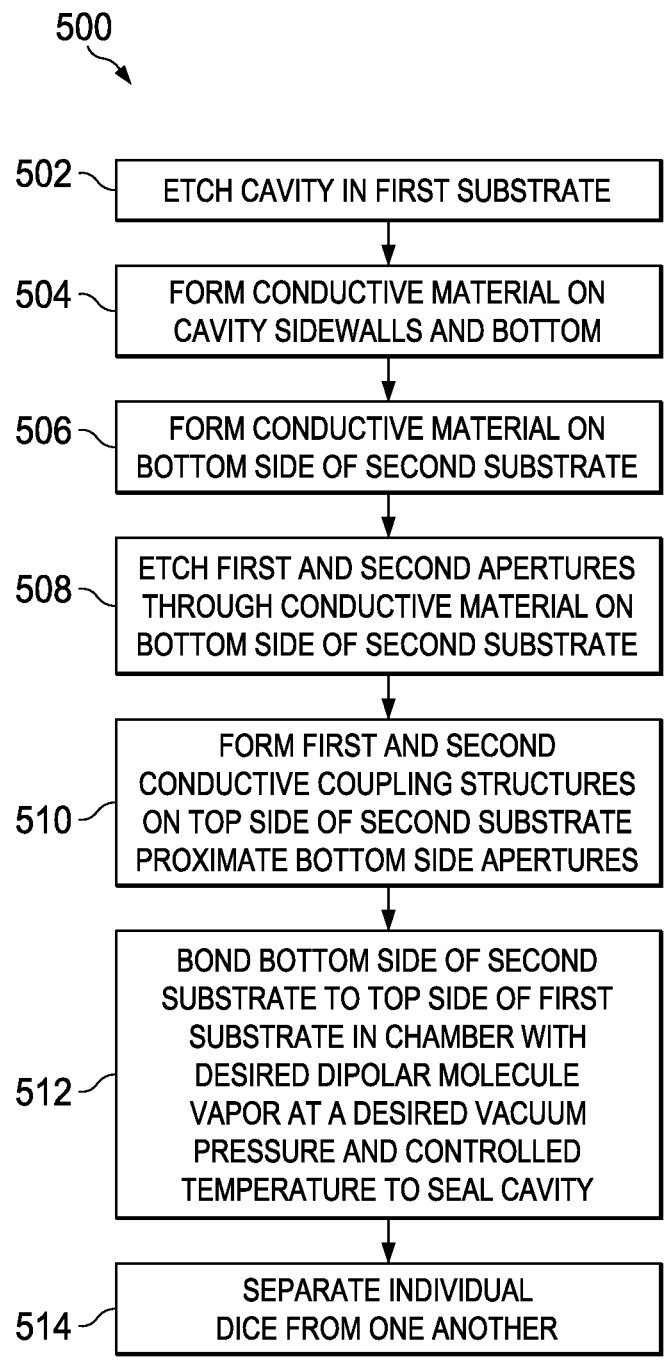
FIG. 5 is a flow diagram showing a method for fabricating a vapor cell.

Referring now to FIGS. 5-15, the inventors have developed wafer scale or chip scale fabrication techniques by which vapor cells 101 and atomic clock systems 100 can be produced using silicon or other semiconductor-based integrated circuit processes for compact, low power, and cost effective solutions. FIG. 5 shows a process or method 500 for fabricating a vapor cell 101, with various interconnection techniques being possible for subsequently integrating the produced vapor cell 101 with a transceiver circuit 130 to provide a clock system 100, and FIGS. 6-15 show the cell 101 at various stages of fabrication processing according to the method 500. The example process 500 facilitates direct packaging of a compact chip scale vapor cell 101 or physics cell having a low-pressure dipolar molecule gas in a mm-wave waveguide cavity 103 which can be packaged with a transceiver die via wire bonding, flip chip, or other packaging techniques.

The process 500 in FIG. 5 begins at 502 with formation of a cavity 103 in a first (e.g., top) side 102a of a first substrate 102. In one example, the first substrate is a silicon wafer. Other substrate materials can be used in different examples, such as glass, etc. Any suitable wet or dry etch processing 602 can be used as shown in FIG. 6 for the cavity formation at 502 in FIG. 5. In some examples, multiple cavities 103 can be formed in a single substrate 102, such as for creating multiple vapor cells 101, with eventual die separation used to separate the individual vapor cells 101 from one another at 514 in FIG. 5. The shape of the cavity 103 is formed at 502 by patterning using a hard mask 604 as shown in FIG. 6. In other examples, a polymeric resist can be used, which is specifically formulated to resist the etchant (e.g., Brewer Science ProTek family of resists) together with bulk anisotropic etching of the silicon substrate 102 via process 602, for example, using strong caustic etchants such as KOH or TMAH.

The etch process 602 forms at least one sidewall 104 along with a cavity bottom 103b having a generally smooth surface, with the process 602 in certain examples providing a cavity bottom and sidewall roughness below about 5 μm RMS for reducing electromagnetically induced current losses in operation of the vapor cell 101. In another example, the etch process 602 etches through the silicon substrate 102 down to a buried etch stop layer (not shown), which may be formed by directly bonding a first substrate comprising silicon to a second substrate (not shown), which may be of silicon or another material (e.g. glass), with a dielectric layer (e.g., silicon dioxide or silicon nitride) therebetween. Such a direct bond may be achieved by several methods known for wafer bonding, where one example uses low-temperature plasma activated fusion bonding for lowest cost and high throughput. After the cavity formation at 502 in FIG. 5 and etch process 602 in FIG. 6, any required mask 604 is removed and clean up processing may be performed.

In some examples, a dielectric layer may be formed on the cavity walls 104 and on the cavity bottom 103b for enhancing the adhesion of subsequently deposited metal materials using any suitable deposition process, such as vapor phase deposition, sputtering, chemical vapor deposition (CVD), atomic layer deposition (ALD), etc, where one suitable dielectric layer is Tantalum pentoxide ($Ta_2O_5$) for good adhesion to copper.

Figure 7:
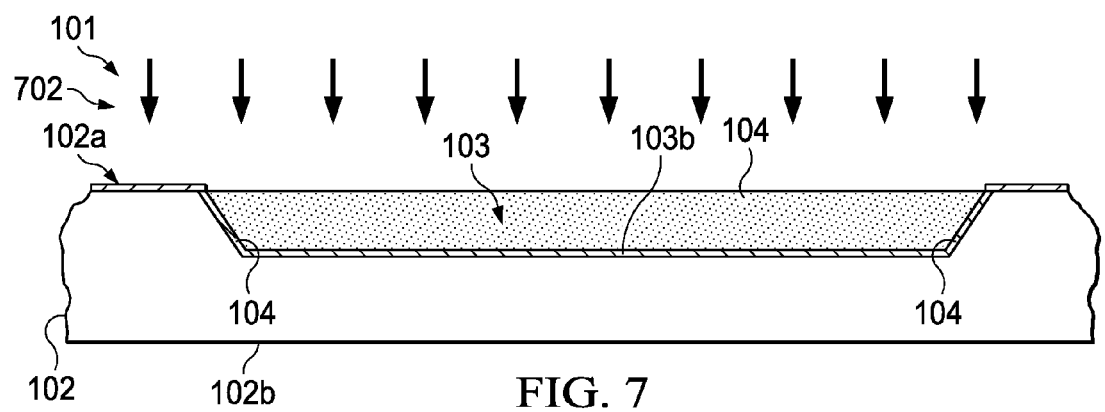
FIG. 7 is a partial side elevation view of the first substrate undergoing a deposition operation to form a conductive material on the cavity bottom and sidewalls.
Figure 8:
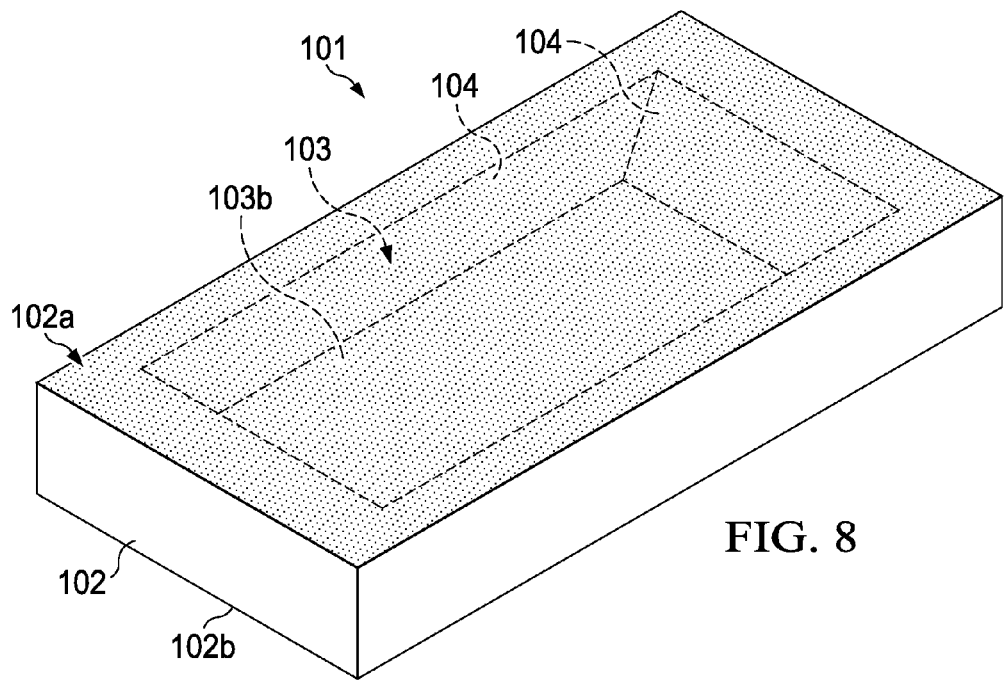
FIG. 8 is a perspective view of the first substrate with a conductive interior cavity surface.

At 504 in FIG. 5, a conductive material 904 is formed directly on the sidewalls 104 and the cavity bottom 103b or over any deposited dielectric layer using any suitable disposition process 702 as shown in FIG. 7. FIG. 8 shows the resulting first substrate 102 following the conductive material deposition process 702 of FIG. 7, with conductive material formed on the sidewalls 104 as well as the cavity bottom 103b and on the top side 102a of the first substrate 102. In one example, the deposited conductive material is copper, and the surface roughness is approximately 100 nm or less for minimizing losses due to currents induced by the electromagnetic field inside the cavity 103.

One suitable deposition process 702 is sputtering of copper metal onto a deposited dielectric layer to provide high conductivity, absence of long-range magnetic order, good adhesion to Ta2O5, and low cost. Other metal materials can be used in different examples, such as those having a similar combination of characteristics. Following sputter deposition in one example, the metal layer may be grown to a desired uniform thickness with copper or any other metal that may be desired, for example, using electroplating for reduced deposition cost. In some examples, the formed metal layer may be coated with a dielectric material via vapor phase deposition or other suitable process, where the optional dielectric material in certain examples may be selected to mitigate reaction of the vapor phase molecules of the vapor cell 101 with the metal layer during the expected product lifetime. Any included dielectric may be removed by patterning and etching from all or a target bonding portion of the top surface 102a of the first substrate 102 to facilitate bonding with a second substrate 106 to close the cavity 103 as described further below. In this example, the conductive material is formed on the sidewalls 104 and the cavity bottom 103b at 504 in FIG. 5 to a thickness greater than the skin depth at the frequency of operation of the finished vapor cell 101, for example, about 100 nm or more and about 1 µm or less to provide a surface roughness of about 50 nm or less for mitigating signal losses in the cavity 103 in one example.

Figure 9:
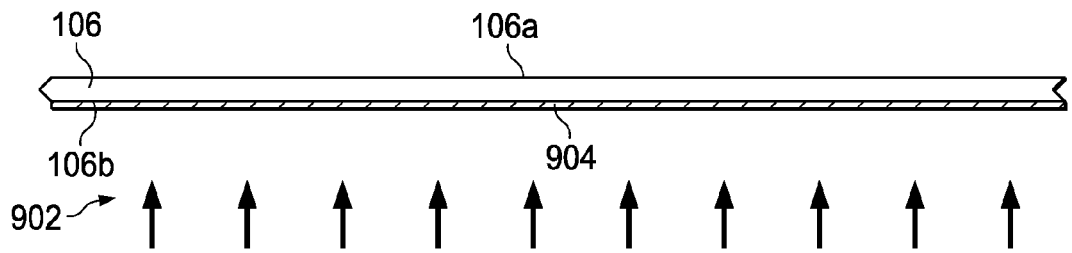
FIG. 9 is a partial side elevation view of a second substrate undergoing a deposition process to form a conductive material on a bottom side thereof.

At 506 in FIG. 5, a second substrate 106 is provided having a first or top side 106a and a second or bottom side 106b. A conductive material 904 is formed on the bottom side 106b of the second substrate 106 using a deposition process 902 as shown in FIG. 9. The second substrate 106 will later be used to form a cavity top through bonding with the first substrate 102, and can be any suitable material, such as a glass or ceramic wafer having a thickness less than a wavelength of the vapor cell operating frequency (e.g., less than 0.5 mm in one example). In practice suitable second substrates 106 are thin enough to facilitate good electromagnetic coupling of microwave energy through the apertures 108 to and from the cavity 103, and thick enough to mitigate or avoid structural distortion when bonded to the first substrate 102 to seal the cavity 103 under vacuum. In this regard, the second substrate material preferably provides good electromagnetic transmissivity through subsequently patterned non-conductive apertures 108 formed in the material 904 as described below. One suitable example material is Corning Eagle XG glass, a low-alkali borosilicate glass available in wafer form of thicknesses ranging from 0.2-3.0 mm. The second substrate 106 in certain examples is coated with a dielectric such as $Ta_2O_5$ on each side 106a and 106b for improving adhesion of metal films which are later formed over the dielectric.

Figure 10:
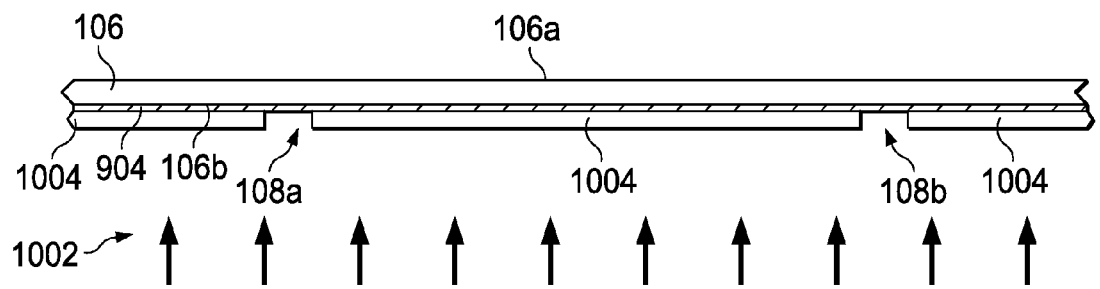
FIG. 10 is a partial side elevation view of the second substrate undergoing an etch process to form non-conductive apertures through the conductive material on the bottom side.

As seen in FIGS. 9-13, the conductive material deposition and patterning can be done separately for the first and second sides 106a and 106b. In one alternate example, the top and bottom sides 106a and 106b can be completely metallized in one step, followed by a subsequent selective patterning to leave the desired conductive and non-conductive regions on both sides 106a and 106b. In the illustrated example, the bottom side 106b is etched at 508 of FIG. 5 via an etch process 1002 using a mask 1004 as shown in FIG. 10 to form first and second spaced apertures 108a and 108b, respectively, through the conductive material 904 on the bottom side 106b, with the remainder of the bottom side 106b remaining coated with the conductive material 904. These apertures or slots 108 form part of the electromagnetic coupling structure that will allow an electromagnetic field to enter and exit the cavity 103 in the finished vapor cell 101 as described above in connection with FIG. 1.

Figure 11:
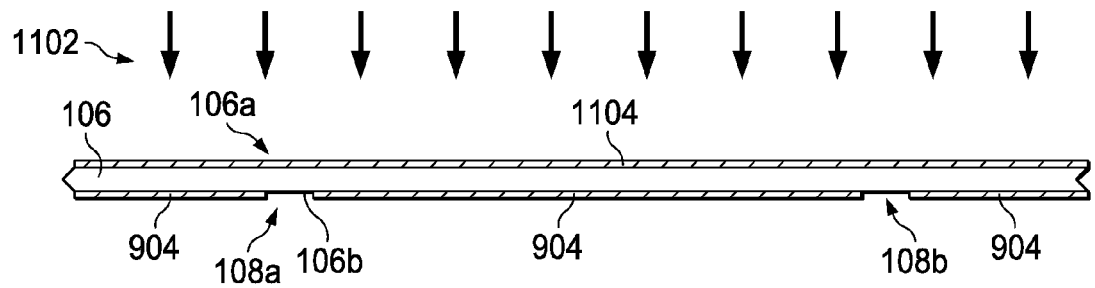
FIG. 11 is a partial side elevation view of the second substrate undergoing a deposition process to form a conductive material on the top side thereof.

Continuing at 510 in FIG. 5, first and second conductive coupling structures 110a and 110b are formed on the first side 106a of the second substrate 106, proximate to the corresponding apertures 108a and 108b formed along the bottom side 106b, as shown in FIGS. 11-14. In FIG. 11, a deposition process 1102 is used to plate the first side 106a with copper or other suitable conductive material 1104, and an etch process 1202 is used with a etch mask 1204 in FIG. 12 to form the first and second copper coupling structures 110a and 110b shown in FIG. 13. As further seen in FIG. 14, the conductive coupling structures 110a and 110b in one example are formed as conductive strips extending longitudinally across the underlying apertures 108a and 108b, respectively, for electromagnetically coupling with the interior of the waveguide cavity 103. In subsequent packaging with a host transceiver 130 (e.g., FIG. 1), the coupling structures 110 can be electrically coupled with the input 133 and 138 using any suitable flip chip, wire bonding, or other electrical interconnection technique to provide a simple and cost-effective packaging assembly with the finished vapor cell structure 101 mounted to a host integrated circuit package or printed circuit board (not shown). In operation, the first coupling structure 110a receives the transmit signal TX from the output 133 of the transceiver 130 and produces a magnetic field which is directed through the aperture 108a to the dipolar molecule gas inside the sealed cavity 103.

Figure 12:
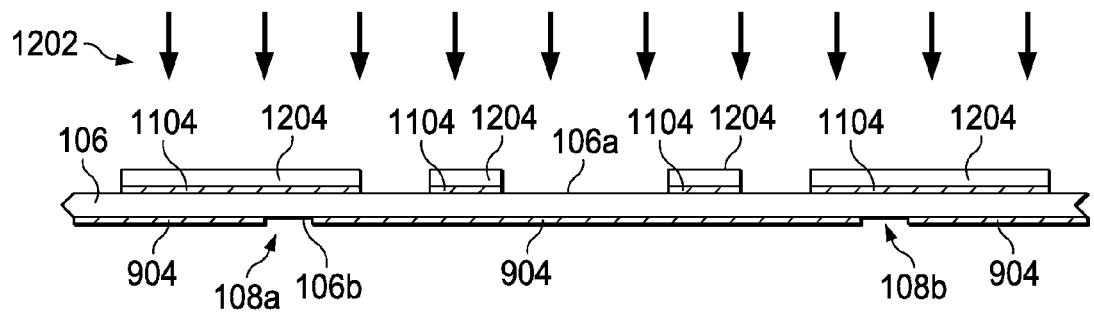
FIG. 12 is a partial side elevation view of the second substrate undergoing an etch process to form first and second conductive coupling structures and electronic bandgap structures on the top side.
Figure 13:
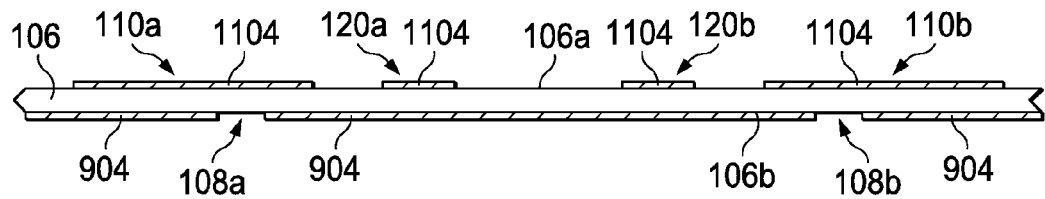
FIG. 13 is a partial side elevation view of the second substrate prior to bonding with the first substrate.
Figure 14:
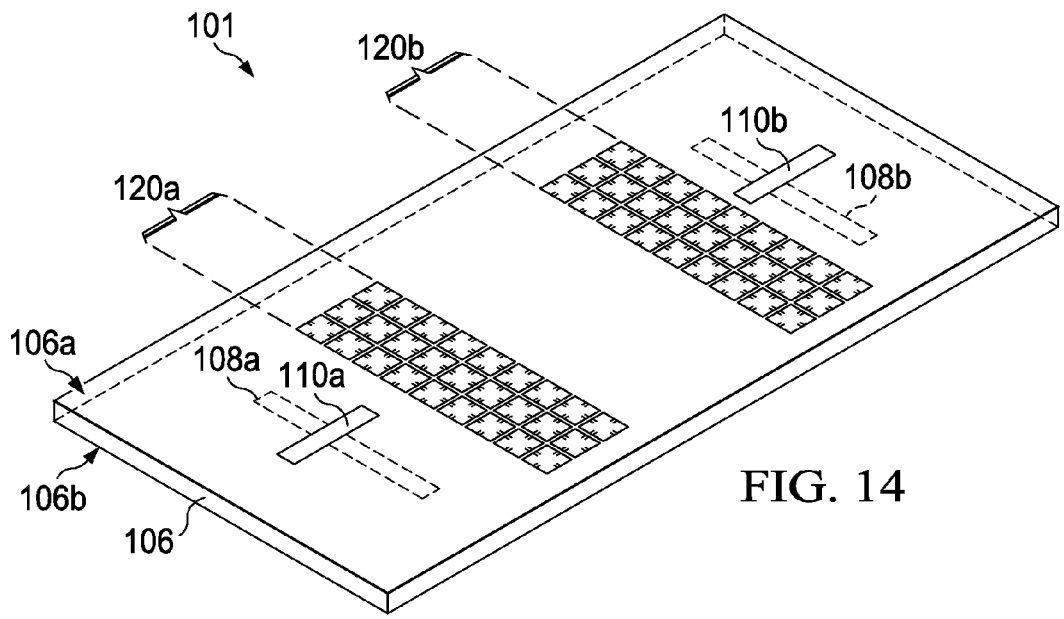
FIG. 14 is a perspective view of the second substrate prior to bonding with the first substrate.

As further shown in FIGS. 12-14, this example also includes patterned conductive electronic bandgap (EBG) structures 120 (FIGS. 13 and 14) formed on the outer surface 106a of the vapor cell 101 via the etch mask 1204 in FIG. 12, where the EBG structures 120 are spaced from the conductive coupling structures 110 in order to avoid or mitigate propagation of spurious surface waves. In the example of FIG. 14, first and second EBG structures 120a and 120b each include three rows of several repeating patterns of conductive material 1104, where any suitable pattern can be used for attenuating electromagnetic wave coupling along the first side 106a of the second substrate 106 of a given target bandgap range of frequencies, with the EBG structures 120 spaced from and disposed between the transmit and receive coupling structures 110a and 110b. In other examples, only a single EBG structure 120 is used, spaced from and between the coupling structures 110a and 110b. Further examples are possible in which more than two EBG structures 120 are provided for attenuating electromagnetic genetic wave coupling along the first side 106a. The EBG structures 120 are omitted in other examples.

As seen in the example second substrate 106 in FIG. 14, the apertures 108 and the coupling structures 110 are both extended rectangular shapes, although other shapes and relative positions can be used in other examples. In various examples, the apertures 108 can be either perpendicular or parallel to the direction of propagation of the TE01 mode within the cavity 103. Because the transceiver circuit 130 provides high frequency TX signals to the vapor cell 101 (e.g., 100-1000 GHz in various examples), and since the second substrate 106 has a thickness of fractions of a wavelength in certain examples, surface waves can propagate along a grounded dielectric slab or along the top surface 106a of the cell 101, and couple between the input and output apertures 108 of the waveguide, thereby creating a second path for the signal which does not pass through the vapor cell cavity 103 and such extra-cavity transmission can mask the absorption of the dipolar molecule gas within the cavity 103 in operation.

Accordingly, some examples include one or more EBG structures 120 to mitigate such surface waves through operation as a photonic bandgap structure. In one example, the EBG structure 120 has a bandgap in an expected operational range of frequencies in order to mitigate or prevent surface wave propagation for example, being tuned to be in the range of frequencies used to interrogate the vapor cell 101. The EBG is a tuned filter including the parallel combination of the conducting layer 904 on the second or bottom side 106b of the second substrate 106 and the patterned array of repeating unit cells 120 on the first or top side 106a. In the illustrated examples, no vias are required, but vias can be used in other examples. In one example, the waveguide cavity 103 is etched with a top width of 1.5 mm and an etch depth of 0.5 mm to provide a propagation constant and cutoff for the first three modes with a first mode beginning at 120 GHz, a second mode at 230 GHz, and a third mode at 290 GHz, and the cavity 103 is designed in one example for operation in a frequency range where only the first mode can propagate (which can be tuned by changing the waveguide dimensions in other examples). In this example, there is a band gap of frequencies ranging from 160-195 GHz at which no mode can propagate along the top side 106a, with the EBG arrays 120 placed between the two ports of the waveguide to prevent a second path for the electromagnetic signal in the bandgap of interest.

Continuing at 512 in FIG. 5, the bottom side 106b of the second substrate 106 is bonded via a bonding process 1500 of FIG. 15 in an ambient environment including a dipolar molecule gas (e.g., $H_2O$) at a low ambient pressure to the first side 102a of the first substrate 102 to form a sealed cavity 103 including the low-pressure dipolar molecular gas $H_2O$. The bonding process 1500 can be any suitable wafer bonding step or steps that does not introduce any unwanted gases inside the cavity 103 and seals the cavity 103 with the low-pressure dipolar molecule vapor. Suitable metal bonding process examples 1500 include forming solid-liquid inter diffusion (SLID) bonds or transient liquid phase (TLP) bonds, for example, formed at one lower temperature and having a remelting temperature much higher than the temperature at which they are formed. Common TLP bonded metal couples include Au/In, Cu/Sn, Sn/Au, Sn/Ag, where the metal couple can be selected for convenience and overall compatibility with the final device geometry. In certain examples, the cavity pressure is in the range of Microtorr to Millitorr, and thus the substrates 102 and 106 are bonded and sealed at 512 in a processing chamber capable of providing and controlling both heat and vacuum. Suitable processing chambers for the bonding process 1500 are commercially available from suppliers such as Electronic Visions Group (EVG), Austria. The substrates 102 and 106 are placed in the chamber, and a suitable vacuum headspace with a small partial pressure of the desired dipole molecule vapor such as water, acetonitrile, methyl fluoride, etc. is established. The substrates 102 and 106 are then bonded according to a corresponding suitable temperature profile for creating an impermeable seal of each separate cavity 103 of a processed wafer, with all cavities being bonded essentially concurrently at the wafer level. In an alternate implementation, the cavities 103 may be sequentially sealed by an apparatus which uses laser radiation to locally heat the bonding regions to the required temperature while maintaining a lower temperature of the surrounding die for mitigating degradation and loss of the volatile species.

At 514 in FIG. 5, the devices containing the desired concentration of low-pressure dipolar molecule gas are cingulated using suitable semiconductor dicing techniques. The finished vapor cells 101 (physical cells) are then available for further processing, for example, pick and place, connection via wire bonding to other microwave devices, etc. for a fully integrated system solution.

Figure 16:
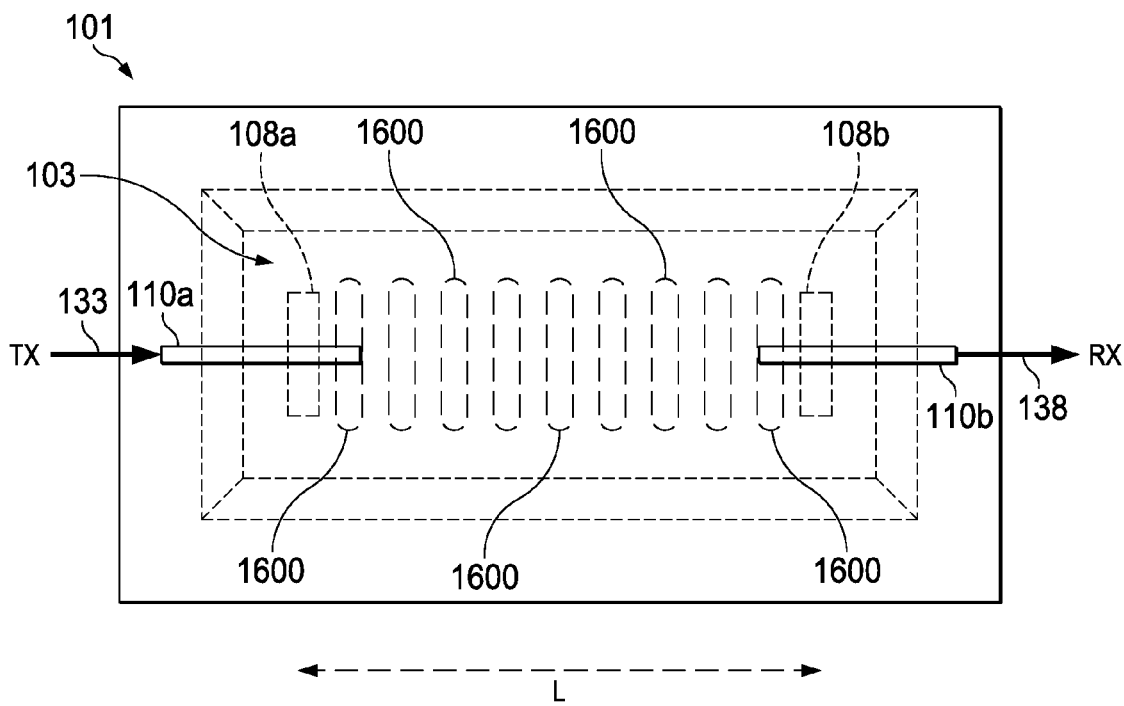
FIG. 16 is a top plan view of the vapor cell apparatus with an electromagnetic field inside the cavity.

FIG. 16 shows a simplified top plan view of the finished single vapor cell apparatus 101 in operation during interrogation via an associated transceiver circuit 130 (e.g., FIG. 1). An alternating electrical output signal TX is provided via the transceiver output 133 to the first conductive coupling structure 110a for coupling the electromagnetic field 1600 to the interior of the cavity 103 via the input aperture 108a. The field 1600 extends along the longitudinal length L of the cavity 103 to the exit aperture 108b for providing an alternating electrical input signal RX to the transceiver input 138 via the second coupling structure 110b. As previously mentioned, the finished vapor cell 101 may include one or more EBG structures 120 (e.g., FIG. 1) disposed along the top side of the cell structure 101 for attenuating electromagnetic waves, which are omitted from FIG. 16 for ease of illustration of the electromagnetic field 1600 within the interior of the cavity 103.

Figure 17:
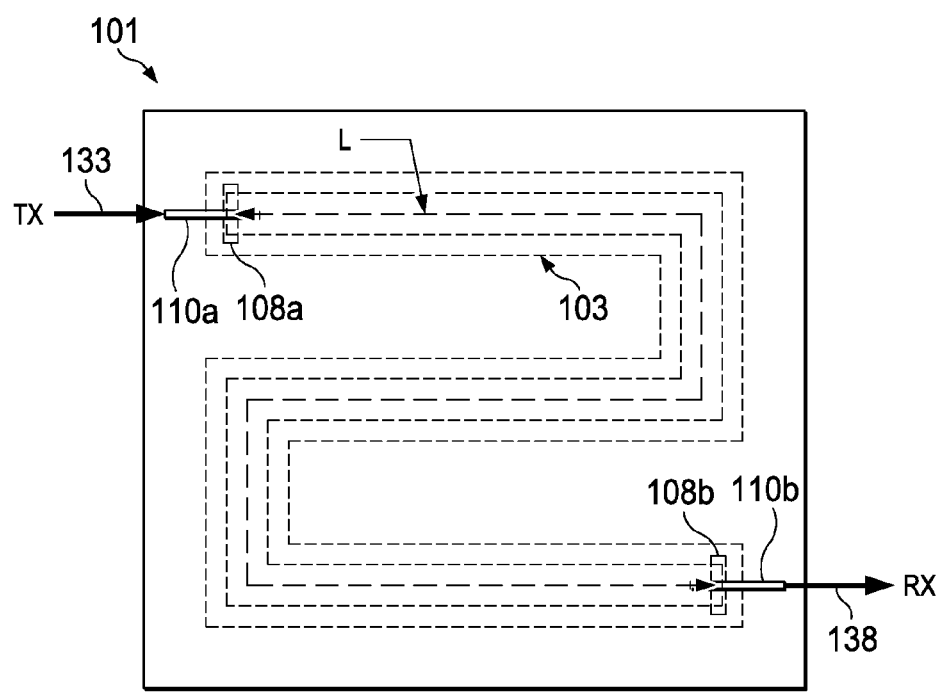
FIG. 17 is a top plan view of another vapor cell with a non-linear cavity.

FIG. 17 shows another vapor cell example 101 constructed using the principles detailed above, in which the cell cavity is meandered along a non-linear path to increase the length and thus the absorption to provide a compact device 101, where the absorption length L in FIG. 17 is longer than that of the cell 101 in FIG. 16, although the overall length of the cell structure 101 is shorter. Other examples are possible including cell cavities 103 extending along linear or non-linear paths, including combinations of linear and non-linear portions, curvilinear portions, stepwise linear portions, and combinations thereof, wherein the present disclosure is not limited to the illustrated examples.

Figure 18:
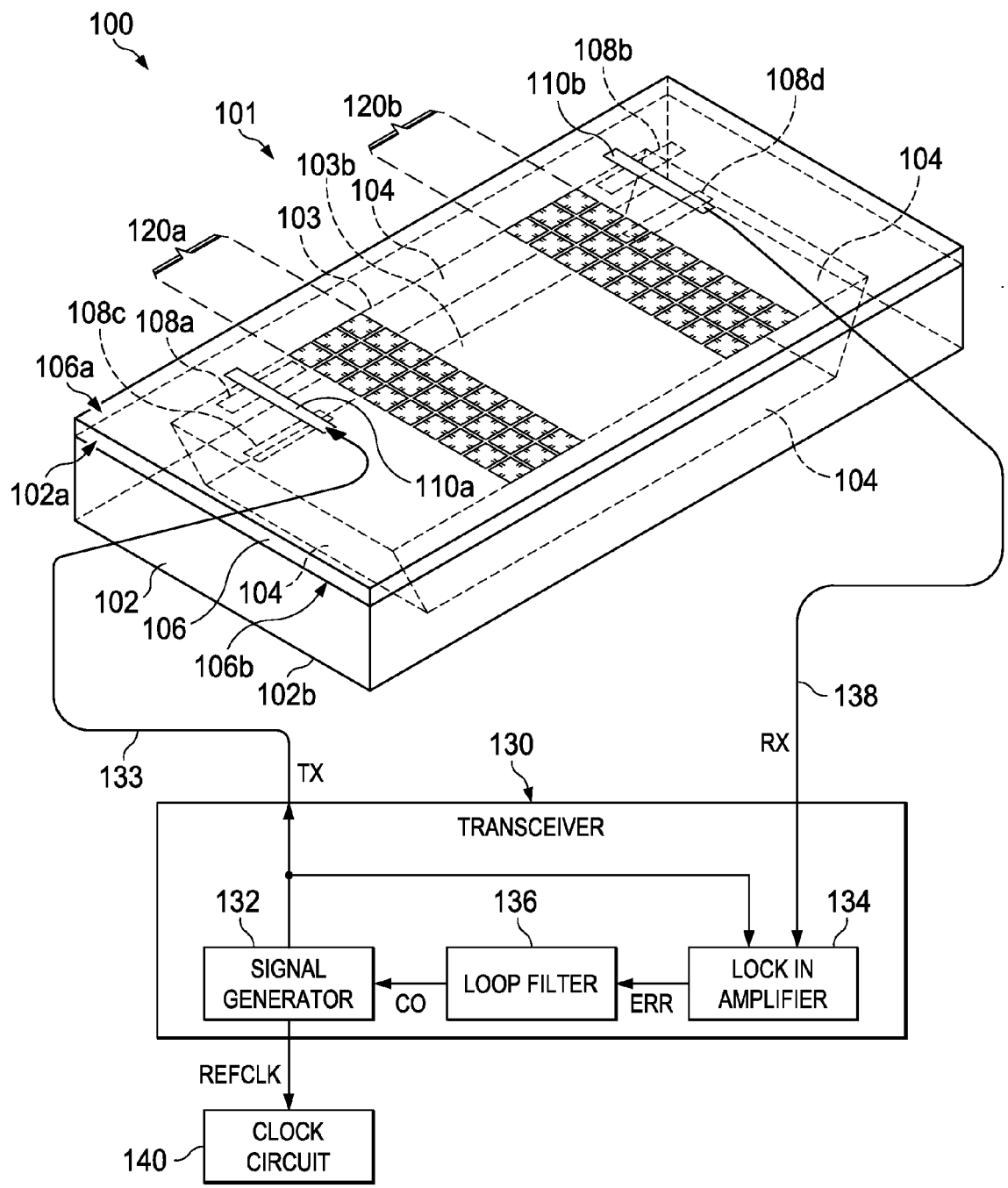
FIG. 18 is a partial perspective view of another rotational transition based atomic clock apparatus having multiple non-conductive apertures and associated conductive coupling structures.

FIG. 18 illustrates another vapor cell example 101 in which the cavity 103 includes third and fourth conductive apertures 108c and 108d, with each conductive coupling structure 110 being proximate a pair of non-conductive apertures. In this example, apertures 108a and 108c are parallel to one another and the corresponding transmit coupling structure 110a extends generally perpendicularly across the parallel pair of apertures 108a and 108c. Similarly, the non-conductive bottom side apertures 108b and 108d are generally parallel to one another, with the associated receive conductive coupling structure 110b extending perpendicular to and over the corresponding receiver apertures 108b and 108d. In this example, the third aperture 108c provides a second electromagnetic field entrance to the cavity 103, and the fourth non-conductive aperture 108d provides another electromagnetic field exit from the cavity 103. Other combinations of one or more apertures 108 with one or more associated conductive coupling structures 110 can be used for electromagnetic coupling with the interior of the cavity 103 in other examples.

The present disclosure thus provides mm-wave atomic clocks 100 and rotational transition vapor cells 101 with simple cost-effective and low power operation using rotational quantum transition of low-pressure gas molecules to provide a reference clock signal REFCLK, while avoiding the complexity, power consumption, cost, and size shortcomings of conventional atomic clocks that use electronic transitions for establishing a reference. The disclosed rotational transition-based atomic clock concepts are stable with temperature variations, and can be manufactured using chip-scale or wafer-scale processing technology. Furthermore, the disclosed clocks 100 operate at much lower frequencies than electronic transition devices to ascertain and lock-in to the rotational quantum state of a low-pressure dipolar molecule vapor, and the disclosed techniques avoid problems associated with providing a clear optical transmission path as in conventional optically interrogated vapor cells. Furthermore, the disclosed vapor cells 101 can be used with a variety of low-cost mm-wave CMOS transceiver circuits 130 to interrogate the low-pressure dipolar molecule gas in the physical cell 101 over a bandwidth which covers the transition. Furthermore, water and other dipole molecule gases exhibit detectable absorption changes at the transition frequency to facilitate lock-in for providing a stable reference clock signal, and the vapor cell 101 and the overall atomic clock system 100 can be constructed and packaged in certain examples within a silicon fabrication and packaging process. Furthermore, the disclosed chip-scale dipolar molecule vapor cells 101 can be used in atomic clocks as well as other applications involving rotational spectroscopy, and provide a more compact design than other rotational spectroscopy solutions.

Modifications are possible in the described embodiments, and other embodiments are possible, within the scope of the claims.

What is claimed is:
1. A clock apparatus, comprising:
   a vapor cell, including:
      a cavity including a sealed interior with a conductive interior cavity surface, a first non-conductive aperture in the interior cavity surface for providing an electromagnetic field entrance to the cavity, and a second non-conductive aperture spaced from the first non-conductive aperture in the interior cavity surface for providing an electromagnetic field exit from the cavity,
      a dipolar molecule gas inside the sealed interior of the cavity,
      a first conductive coupling structure formed on an outer surface of the vapor cell proximate the first non-conductive aperture, and
      a second conductive coupling structure formed on the outer surface of the vapor cell proximate the second non-conductive aperture; and
   a transceiver circuit for providing an alternating electrical output signal to the first conductive coupling structure for coupling an electromagnetic field to the interior of the cavity, for receiving an alternating electrical input signal from the second conductive coupling structure representing the electromagnetic field received from the cavity, for selectively adjusting a frequency of the electrical output signal to reduce the electrical input signal, and for providing a reference clock signal at the frequency of the electrical output signal;
   wherein the cavity extends along a non-linear axis from a first end to a second end, wherein the first non-conductive aperture is proximate the first end, and wherein the second non-conductive aperture is proximate the second end.
2. A clock apparatus, comprising:
   a vapor cell, including:
      a cavity including a sealed interior with a conductive interior cavity surface, a first non-conductive aperture in the interior cavity surface for providing an electromagnetic field entrance to the cavity, and a second non-conductive aperture spaced from the first non-conductive aperture in the interior cavity surface for providing an electromagnetic field exit from the cavity,
      a dipolar molecule gas inside the sealed interior of the cavity,
      a first conductive coupling structure formed on an outer surface of the vapor cell proximate the first non-conductive aperture, and
      a second conductive coupling structure formed on the outer surface of the vapor cell proximate the second non-conductive aperture; and
   a transceiver circuit for providing an alternating electrical output signal to the first conductive coupling structure for coupling an electromagnetic field to the interior of the cavity, for receiving an alternating electrical input signal from the second conductive coupling structure representing the electromagnetic field received from the cavity, for selectively adjusting a frequency of the electrical output signal to reduce the electrical input signal, and for providing a reference clock signal at the frequency of the electrical output signal;
   wherein the cavity includes a third non-conductive aperture spaced from the first non-conductive aperture in the interior cavity surface for providing another electromagnetic field entrance to the cavity, and a fourth non-conductive aperture spaced from the second non-conductive aperture in the interior cavity surface for providing another electromagnetic field exit from the cavity; wherein the first conductive coupling structure is proximate the first and third non-conductive; and wherein the second conductive coupling structure is proximate the second and fourth non-conductive apertures.
3. A clock apparatus, comprising:
   a vapor cell, including:
      a cavity including a sealed interior with a conductive interior cavity surface, a first non-conductive aperture in the interior cavity surface for providing an electromagnetic field entrance to the cavity, and a second non-conductive aperture spaced from the first non-conductive aperture in the interior cavity surface for providing an electromagnetic field exit from the cavity,
      a dipolar molecule gas inside the sealed interior of the cavity,
      a first conductive coupling structure formed on an outer surface of the vapor cell proximate the first non-conductive aperture, and
      a second conductive coupling structure formed on the outer surface of the vapor cell proximate the second non-conductive aperture;
   a transceiver circuit for providing an alternating electrical output signal to the first conductive coupling structure for coupling an electromagnetic field to the interior of the cavity, for receiving an alternating electrical input signal from the second conductive coupling structure representing the electromagnetic field received from the cavity, for selectively adjusting a frequency of the electrical output signal to reduce the electrical input signal, and for providing a reference clock signal at the frequency of the electrical output signal; and
   at least one conductive electronic bandgap structure formed on the outer surface of the vapor cell spaced from and between the first and second conductive coupling structures for attenuating electromagnetic wave coupling along the outer surface of the vapor cell.
4. A clock apparatus, comprising:
   a vapor cell, including:
      a cavity including a sealed interior with a conductive interior cavity surface, a first non-conductive aperture in the interior cavity surface for providing an electromagnetic field entrance to the cavity, and a second non-conductive aperture spaced from the first non-conductive aperture in the interior cavity surface for providing an electromagnetic field exit from the cavity,
a dipolar molecule gas inside the sealed interior of the cavity,
a first conductive coupling structure formed on an outer surface of the vapor cell proximate the first non-conductive aperture, and
a second conductive coupling structure formed on the outer surface of the vapor cell proximate the second non-conductive aperture; and
a transceiver circuit for providing an alternating electrical output signal to the first conductive coupling structure for coupling an electromagnetic field to the interior of the cavity, for receiving an alternating electrical input signal from the second conductive coupling structure representing the electromagnetic field received from the cavity, for selectively adjusting a frequency of the electrical output signal to reduce the electrical input signal, and for providing a reference clock signal at the frequency of the electrical output signal;
wherein the transceiver circuit includes:
a signal generator with an output electrically coupled with the first conductive coupling structure for providing the alternating electrical output signal to the first conductive coupling structure and for providing the reference clock signal at the frequency of the electrical output signal;
a lock-in amplifier with an input electrically coupled with the second conductive coupling structure for receiving the alternating electrical input signal and providing an error signal representing a difference between the electrical input signal and the electrical output signal; and
a loop filter for receiving the error signal and providing a control output signal to the signal generator for selectively adjusting the frequency of the electrical output signal to maintain the frequency of the electrical output signal at a peak absorption frequency of the dipolar molecule gas inside the sealed interior of the cavity.

5. A clock apparatus, comprising:
a vapor cell, including:
a cavity including a sealed interior with a conductive interior cavity surface, a first non-conductive aperture in the interior cavity surface for providing an electromagnetic field entrance to the cavity, and a second non-conductive aperture spaced from the first non-conductive aperture in the interior cavity surface for providing an electromagnetic field exit from the cavity,
a dipolar molecule gas inside the sealed interior of the cavity,
a first conductive coupling structure formed on an outer surface of the vapor cell proximate the first non-conductive aperture, and
a second conductive coupling structure formed on the outer surface of the vapor cell proximate the second non-conductive aperture; and
a transceiver circuit for providing an alternating electrical output signal to the first conductive coupling structure for coupling an electromagnetic field to the interior of the cavity, for receiving an alternating electrical input signal from the second conductive coupling structure representing the electromagnetic field received from the cavity, for selectively adjusting a frequency of the electrical output signal to reduce the electrical input signal, and for providing a reference clock signal at the frequency of the electrical output signal;
wherein the vapor cell includes: a first substrate including a first side, at least one cavity sidewall extending inward of the first side, and a cavity bottom; and a second substrate including a first side and a second side including a cavity top, the second side of the second substrate mounted to the first side of the first substrate to form the cavity including the sealed interior with the conductive interior cavity surface extending at least partially along the at least one cavity sidewall, the cavity bottom, and the second side of the second substrate;
wherein the first and second non-conductive apertures are formed in the interior cavity surface on the second side of the second substrate for providing the electromagnetic field entrance and exit, respectively; and
wherein the first and second conductive coupling structures are formed on the first side of the second substrate.

6. A clock apparatus, comprising:
a vapor cell, including:
a cavity including a sealed interior with a conductive interior cavity surface, a first non-conductive aperture in the interior cavity surface for providing an electromagnetic field entrance to the cavity, and a second non-conductive aperture spaced from the first non-conductive aperture in the interior cavity surface for providing an electromagnetic field exit from the cavity,
a dipolar molecule gas inside the sealed interior of the cavity,
a first conductive coupling structure formed on an outer surface of the vapor cell proximate the first non-conductive aperture, and
a second conductive coupling structure formed on the outer surface of the vapor cell proximate the second non-conductive aperture; and
a transceiver circuit for providing an alternating electrical output signal to the first conductive coupling structure for coupling an electromagnetic field to the interior of the cavity, for receiving an alternating electrical input signal from the second conductive coupling structure representing the electromagnetic field received from the cavity, for selectively adjusting a frequency of the electrical output signal to reduce the electrical input signal, and for providing a reference clock signal at the frequency of the electrical output signal;
wherein the dipolar molecule gas is at a pressure of approximately 1 mbar or less inside the sealed interior of the cavity.

7. The clock apparatus of claim 6, wherein the dipolar molecule gas is at a pressure of approximately 0.1 mbar or less inside the sealed interior of the cavity; and wherein the dipolar molecule gas is at a pressure of approximately 0.01 mbar or more inside the sealed interior of the cavity.

8. A clock apparatus, comprising:
a vapor cell, including:
a cavity including a sealed interior with a conductive interior cavity surface, a first non-conductive aperture in the interior cavity surface for providing an electromagnetic field entrance to the cavity, and a second non-conductive aperture spaced from the first non-conductive aperture in the interior cavity surface for providing an electromagnetic field exit from the cavity, a dipolar molecule gas inside the sealed interior of the cavity, a first conductive coupling structure formed on an outer surface of the vapor cell proximate the first non-conductive aperture, and a second conductive coupling structure formed on the outer surface of the vapor cell proximate the second non-conductive aperture; and a transceiver circuit for providing an alternating electrical output signal to the first conductive coupling structure for coupling an electromagnetic field to the interior of the cavity, for receiving an alternating electrical input signal from the second conductive coupling structure representing the electromagnetic field received from the cavity, for selectively adjusting a frequency of the electrical output signal to reduce the electrical input signal, and for providing a reference clock signal at the frequency of the electrical output signal;

wherein the conductive interior cavity surface is plated with a metal material extending at least partially along the at least one cavity sidewall, the cavity bottom, and the second side of the second substrate, the metal material having a thickness greater than a skin depth at the frequency of the electrical output signal.

9. A vapor cell, comprising:

a cavity formed in at least one substrate, the cavity including a sealed interior with a conductive interior cavity surface, a first non-conductive aperture in the interior cavity surface for providing an electromagnetic field entrance to the cavity, and a second non-conductive aperture spaced from the first non-conductive aperture in the interior cavity surface for providing an electromagnetic field exit from the cavity;

a dipolar molecule gas inside the sealed interior of the cavity;

a first conductive coupling structure formed on an outer surface of the vapor cell proximate the first non-conductive aperture; and a second conductive coupling structure formed on the outer surface of the vapor cell proximate the second non-conductive aperture;

wherein the cavity extends along a non-linear axis from a first end to a second end, wherein the first non-conductive aperture is proximate the first end, and wherein the second non-conductive aperture is proximate the second end.

10. A vapor cell, comprising:

a cavity formed in at least one substrate, the cavity including a sealed interior with a conductive interior cavity surface, a first non-conductive aperture in the interior cavity surface for providing an electromagnetic field entrance to the cavity, and a second non-conductive aperture spaced from the first non-conductive aperture in the interior cavity surface for providing an electromagnetic field exit from the cavity;

a dipolar molecule gas inside the sealed interior of the cavity;

a first conductive coupling structure formed on an outer surface of the vapor cell proximate the first non-conductive aperture; and a second conductive coupling structure formed on the outer surface of the vapor cell proximate the second non-conductive aperture;

wherein the cavity includes a third non-conductive aperture spaced from the first non-conductive aperture in the interior cavity surface for providing another electromagnetic field entrance to the cavity, and a fourth non-conductive aperture spaced from the second non-conductive aperture in the interior cavity surface for providing another electromagnetic field exit from the cavity; wherein the first conductive coupling structure is proximate the first and third non-conductive apertures; and wherein the second conductive coupling structure is proximate the second and fourth non-conductive apertures.

11. A vapor cell, comprising:

a cavity formed in at least one substrate, the cavity including a sealed interior with a conductive interior cavity surface, a first non-conductive aperture in the interior cavity surface for providing an electromagnetic field entrance to the cavity, and a second non-conductive aperture spaced from the first non-conductive aperture in the interior cavity surface for providing an electromagnetic field exit from the cavity;

a dipolar molecule gas inside the sealed interior of the cavity;

a first conductive coupling structure formed on an outer surface of the vapor cell proximate the first non-conductive aperture;

a second conductive coupling structure formed on the outer surface of the vapor cell proximate the second non-conductive aperture; and at least one conductive electronic bandgap structure formed on the outer surface of the vapor cell spaced from and between the first and second conductive coupling structures for attenuating electromagnetic wave coupling along the outer surface of the vapor cell.

12. A vapor cell, comprising:

a cavity formed in at least one substrate, the cavity including a sealed interior with a conductive interior cavity surface, a first non-conductive aperture in the interior cavity surface for providing an electromagnetic field entrance to the cavity, and a second non-conductive aperture spaced from the first non-conductive aperture in the interior cavity surface for providing an electromagnetic field exit from the cavity;

a dipolar molecule gas inside the sealed interior of the cavity;

a first conductive coupling structure formed on an outer surface of the vapor cell proximate the first non-conductive aperture;

a second conductive coupling structure formed on the outer surface of the vapor cell proximate the second non-conductive aperture;

a first substrate including a first side, at least one cavity sidewall extending inward of the first side, and a cavity bottom; and a second substrate including a first side and a second side including a cavity top, the second side of the second substrate mounted to the first side of the first substrate to form the cavity including the sealed interior with the conductive interior cavity surface extending at least partially along the at least one cavity sidewall, the cavity bottom, and the second side of the second substrate;

wherein the first and second non-conductive apertures are formed in the interior cavity surface on the second side of the second substrate for providing the electromagnetic field entrance and exit, respectively; and wherein the first and second conductive coupling structures are formed on the first side of the second substrate.

13. A vapor cell, comprising:
a cavity formed in at least one substrate, the cavity including a sealed interior with a conductive interior cavity surface, a first non-conductive aperture in the interior cavity surface for providing an electromagnetic field entrance to the cavity, and a second non-conductive aperture spaced from the first non-conductive aperture in the interior cavity surface for providing an electromagnetic field exit from the cavity;
a dipolar molecule gas inside the sealed interior of the cavity;
a first conductive coupling structure formed on an outer surface of the vapor cell proximate the first non-conductive aperture; and
a second conductive coupling structure formed on the outer surface of the vapor cell proximate the second non-conductive aperture;
wherein the dipolar molecule gas is at a pressure of approximately 1 mbar or less inside the sealed interior of the cavity.

14. The vapor cell of claim 13, wherein the dipolar molecule gas is at a pressure of approximately 0.1 mbar or less inside the sealed interior of the cavity; and wherein the dipolar molecule gas is at a pressure of approximately 0.01 mbar or more inside the sealed interior of the cavity.

15. A vapor cell, comprising:
a cavity formed in at least one substrate, the cavity including a sealed interior with a conductive interior cavity surface, a first non-conductive aperture in the interior cavity surface for providing an electromagnetic field entrance to the cavity, and a second non-conductive aperture spaced from the first non-conductive aperture in the interior cavity surface for providing an electromagnetic field exit from the cavity;
a dipolar molecule gas inside the sealed interior of the cavity;
a first conductive coupling structure formed on an outer surface of the vapor cell proximate the first non-conductive aperture; and
a second conductive coupling structure formed on the outer surface of the vapor cell proximate the second non-conductive aperture;
wherein the conductive interior cavity surface is plated with a metal material having a thickness greater than a skin depth at the frequency of the electrical output signal.

* * * * *